(12) United States Patent
Panagopoulou et al.

(10) Patent No.: US 11,504,444 B2
(45) Date of Patent: Nov. 22, 2022

(54) MODIFIED LIQUID ELECTRICAL VAPORISER

(71) Applicant: Reckitt Benckiser (Brands) Limited, Slough (GB)

(72) Inventors: Dafni Panagopoulou, Hull (GB); Simon Woolley, Hull (GB)

(73) Assignee: Reckitt Benckiser (Brands) Limited, Slough (GB)

( * ) Notice: Subject to any disclaimer, the term of this patent is extended or adjusted under 35 U.S.C. 154(b) by 415 days.

(21) Appl. No.: 16/632,047

(22) PCT Filed: Aug. 21, 2018

(86) PCT No.: PCT/GB2018/052364
§ 371 (c)(1),
(2) Date: Jan. 17, 2020

(87) PCT Pub. No.: WO2019/038529
PCT Pub. Date: Feb. 28, 2019

(65) Prior Publication Data
US 2020/0171190 A1    Jun. 4, 2020

(30) Foreign Application Priority Data
Aug. 23, 2017    (GB) ...................... 1713523

(51) Int. Cl.
*A61L 9/03* (2006.01)
(52) U.S. Cl.
CPC ......... *A61L 9/037* (2013.01); *A61L 2209/133* (2013.01); *A61L 2209/134* (2013.01); *A61L 2209/15* (2013.01)

(58) Field of Classification Search
CPC ............... A61L 9/037; A61L 2209/133; A61L 2209/134; A61L 2209/15
See application file for complete search history.

(56) References Cited

U.S. PATENT DOCUMENTS

| | | | |
|---|---|---|---|
| 6,779,905 B1 * | 8/2004 | Mazursky | ................ F21V 1/10 362/86 |
| 8,603,398 B2 | 12/2013 | Broncano Atencia et al. | |
| 2005/0180736 A1 | 8/2005 | Zobele et al. | |
| 2008/0279731 A1 * | 11/2008 | Goreham | ................ A61L 9/037 422/123 |
| 2008/0315006 A1 | 12/2008 | Belongia et al. | |
| 2010/0221143 A1 | 9/2010 | Lee et al. | |

(Continued)

FOREIGN PATENT DOCUMENTS

| | | |
|---|---|---|
| DE | 202010005923 U1 | 9/2010 |
| EP | 1627648 B1 | 8/2010 |
| RU | 2323008 C2 | 6/2006 |

(Continued)

OTHER PUBLICATIONS

International Search Report and Written Opinion of the International Searching Authority for corresponding application PCT/GB2018/052364 dated Nov. 8, 2018.

(Continued)

*Primary Examiner* — Timothy C Cleveland
(74) *Attorney, Agent, or Firm* — Norris McLaughlin PA

(57) ABSTRACT

A modified liquid electrical vaporiser is disclosed with a modified chimney that provides enhanced distribution of actives.

17 Claims, 8 Drawing Sheets

(56) References Cited

U.S. PATENT DOCUMENTS

2012/0237404 A1  9/2012  Woolley et al.

FOREIGN PATENT DOCUMENTS

| WO | 2007045835 A2 | 4/2007 |
| WO | 2009027668 A1 | 3/2009 |
| WO | 2011045615 A1 | 4/2011 |
| WO | 2012176003 A1 | 12/2012 |
| WO | 2013173830 A1 | 11/2013 |
| WO | 2015107036 A2 | 7/2015 |
| WO | 2018067347 A1 | 4/2018 |

OTHER PUBLICATIONS

GB Search Report for corresponding application GB 1713523.7 dated Feb. 23, 2018.
English translation of RU Search Report for corresponding application RU 2020111561 dated Nov. 16, 2021.

* cited by examiner

MODIFIED LIQUID ELECTRICAL VAPORISER

This is an application filed under 35 USC 371 based on PCT/GB2018/052364 filed 21, Aug. 2018, which in turn is based on GB 1713523.7 filed 23, Aug. 2017. The present application claims the full priority benefit of these prior applications and herein incorporates by reference the full disclosures of these prior applications.

Liquid electrical vaporisers are popular devices with consumers. They typically consist of a housing with plug to connect to mains electricity supply, a heater, a wick or other liquid transfer mechanism and a detachable refill bottle of a volatile liquid containing an active. Usually the wick forms part of the refill bottle and is designed such that on insertion into the housing the wick is in close proximity to the heater.

The actives in the solutions typically used with liquid electrical vaporisers, are medicaments, insecticides and fragrances.

A typical commercial example would be Air Wick's® plug in devices. These are used to provide fragrance release.

Once turned on and up to operating temperature, they can provide a steady, low or high level as desired, emanation of volatile active over days, weeks or months.

One of the drawbacks of these devices is they can take some time to reach ideal and steady state emanating conditions from cold. This can lead consumers to incorrectly believe they are not functioning properly. Another drawback is that as the fragrance exits the top of the device it is attracted to the adjacent wall, rather than emanating throughout the room.

It is the object of the present invention to improve these aspects of liquid electrical vaporisers. Specifically, the present invention effectively both draws the active laden air into the room and reduces the time taken to achieve noticeable levels of the active in a room. Furthermore, the present invention results in a uniform distribution of fragrance within a room and avoids the staining of walls with fragrance.

In a first aspect of the invention there is provided a liquid electric vaporizer comprising;
a housing;
a plug, suitable for engaging with a mains electricity socket, located on one side of the housing;
a chimney, wherein the chimney comprises an inner surface and an external opening at the top of the housing; and further wherein the chimney has a side proximal to the plug and a side that is distal to the plug;
a heating means, located adjacent the chimney;
a detachable refill bottle which engages with the housing, the refill bottle having a wick in fluid communication with a material to be dispensed therefrom; and
the wick extending from the bottle into the chimney in proximity with said heating means when the refill bottle is engaged with the housing;
wherein the external opening of the chimney is non-regular, such that the chimney extends further on the side of the device that is distal to the plug than the side that is proximal to the plug, to form a distal chimney extension.

FIG. 1 shows the device with the refill 4 in place.

FIG. 2 shows the device 1 and refill 4 separately immediately prior to engaging the refill with the device housing.

Figure 1:
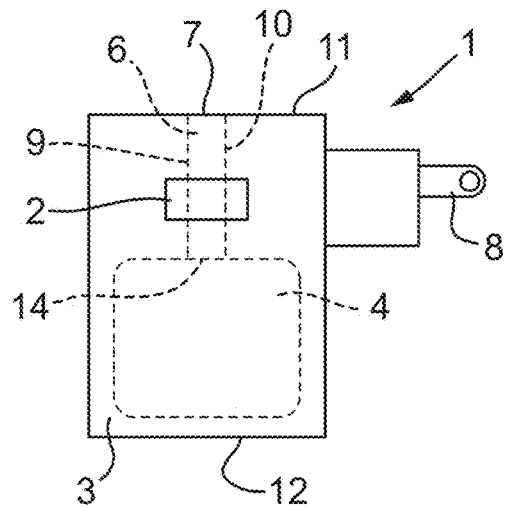
FIGS. 1 and 2 show a schematic of a standard or prior art liquid electrical vaporiser.
Figure 2:
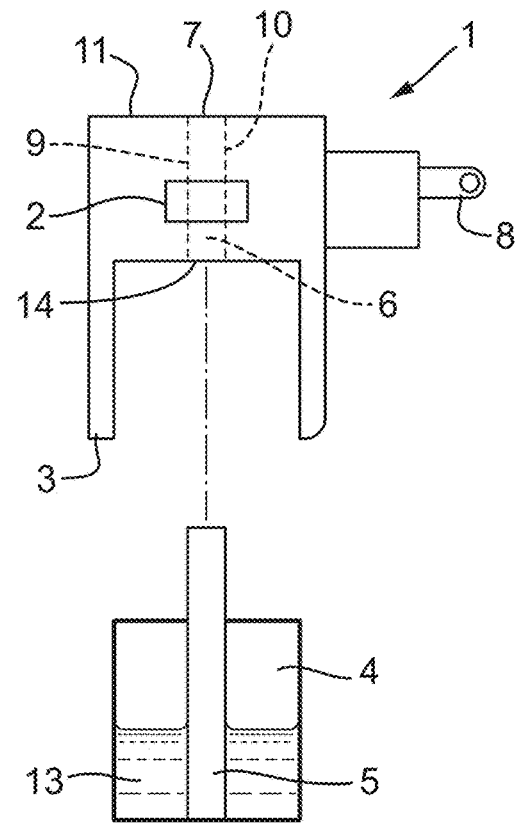

Liquid electrical device 1 has an eternal housing 3. A mains plug 8 is attached to the housing 3 to provide power for the heater 2, which is located adjacent chimney 6. The housing 3 has a top surface 11 and a bottom surface 12. The housing also contains space for the refill 4 to be connected to the housing. A wick 5 that protrudes from refill 4 is designed to fit within the chimney 6 close to the heater 2, such that liquid active composition 13 is drawn up through the wick 5 and evaporated off when the device is in use. The chimney 6 has an opening 7 through which the vaporised active leaves the device. The chimney has a side 10 that is proximal to the plug 8 and a side 9 that is distal to the plug 8.

Figure 3:
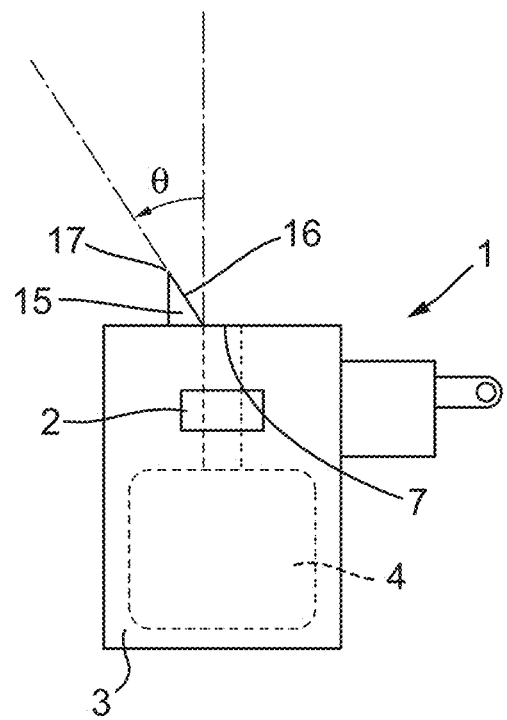
Figure 5:
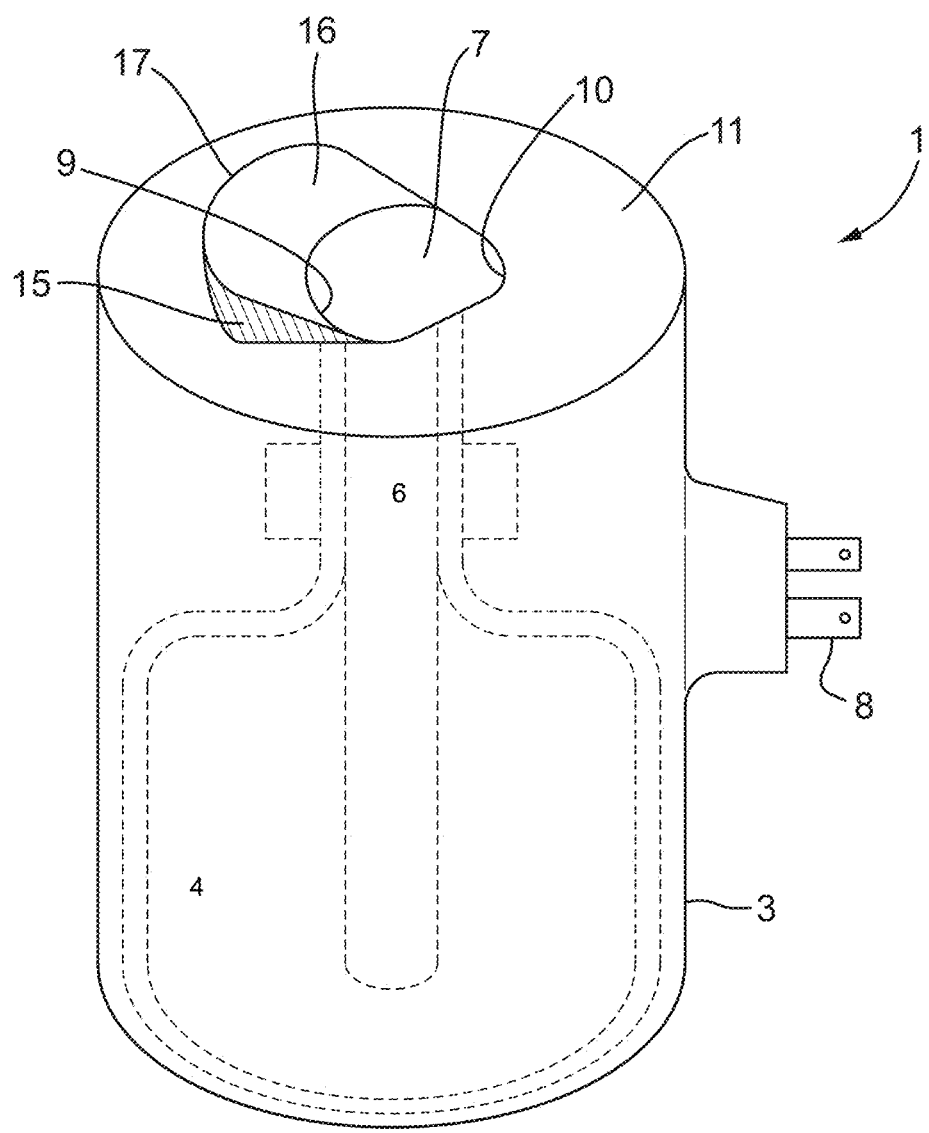

FIGS. 3 and 5 show two schematics of a liquid electrical vaporiser 1 according to the present invention. The primary difference from devices known in the art is the inclusion of a distal chimney extension 15. This means the chimney extends on the side 9 that is distal to the plug 8.

The applicants have found that by providing a distal chimney extension 15 it is possible to draw the warmed and active laden air further into the room (i.e. away from the wall) than using a normal chimney arrangement.

The present invention also distributes the active laden air more uniformly than devices known in the art. The present invention advantageously distributes active laden air at least 10% more uniformly, such as at least 12%, 15% or even 20%, more uniformly than devices known in the art.

Without wishing to be bound by theory, the applicants believe the Coandă effect is responsible for providing the benefit. The Coandă effect is the tendency of a jet of a fluid or gas emerging from an orifice to follow an adjacent flat or curved surface and to entrain fluid from the surroundings so that a region of lower pressure develops. Thus, in the present invention the active laden air is redirected away from the adjacent wall.

In a further aspect of the invention the distal chimney extension 15 is angled away from the vertical plane when the device is plugged in. in contrast, the chimney 6 and opening 7 features of the devices of the art are substantially straight sided and substantially vertical when the devices are plugged into a mains socket. It is preferably that the distal chimney extension 15 is angled away from the plug 8 and into the room to draw the active laden air into the room.

This effect speeds the spread of the active into the room as it pushes the active laden air away from the wall and towards the middle of the room. This allows the active to distribute more quickly into the room.

In a further aspect of the invention the angle θ of the chimney extension away from the vertical plane is at least 15 degrees, preferably at least 25 degrees, more preferably at least 30 degrees and most preferably at least 40 degrees.

Preferably, the chimney extension is rounded at its peak, i.e. the highest point. In other words, the peak does not end sharply with a vertical surface, but is rounded and slopes towards the perimeter of the device. It is believed that such an arrangement aids the surface friction of the fluid (such as active-laden fragrance) leaving the device.

FIG. 3 shows how the angle θ of the distal chimney extension from the chimney direction is measured.

In a further aspect of the invention the distal chimney extension has a convex inner surface.

In a further aspect of the invention the distal chimney extension has a flat inner surface.

The Coandă effect is known to work over both curved and flat surfaces. The overall external shape of the distal chimney extension can be any that achieves the desired effect.

The distal chimney extension may be of varying lengths. Generally, the shorter the distal chimney extension, the less effect it has in drawing the active laden air out into the room.

In a further aspect of the invention the distal chimney extension between opening 7 and distal chimney extension top 17 when measured along distal chimney extension surface 16, is between 5 and 50% of the length of the chimney from the base 14 to the external opening 7, preferably between 3 and 25% of the length of the chimney, more preferably between 5 and 20% of the length of the chimney and most preferably between 7 and 15% of the length of the chimney.

FIG. 1 shows the points between which the chimney length is measured. This is from the base 14 to the lowest point of the opening 7. The lowest point of the opening 7 should be on the proximal chimney side 10.

In a further aspect of the invention the distal chimney extension top 17 extends between 1 mm and 150 mm in vertical height beyond the regular chimney end, chimney opening 7 or top surface 11. Preferably the distal chimney extension top 17 is between 5 mm and 100 mm, more preferably between 7 mm and 50 mm and most preferably between 10 mm and 25 mm higher than chimney opening 7 or top surface 11.

The distal chimney extension 15 may also vary in width or diameter of the chimney 6 that is extended.

In a further aspect of the invention the distal chimney opening 7 comprises at least 30% of the diameter of the chimney 6, preferably at least 40%, 50%, 60%, 70%, or 80% of the diameter of the chimney 6 or even 100% of the diameter of the chimney 6.

Figure 4:
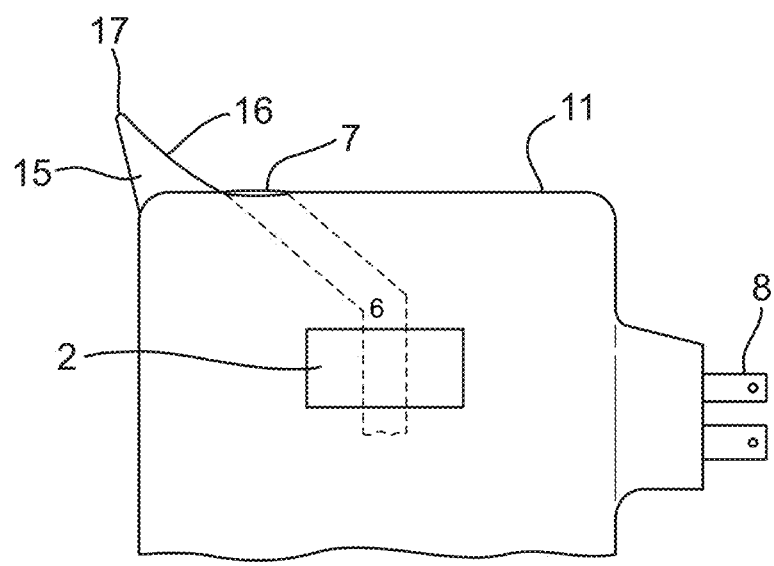

FIG. 4 shows an alternative embodiment where there is a slight 'misalignment' between the distal chimney opening 7 and the chimney 6. Such a misalignment is preferably misaligned in the direction of the room (i.e. away from the plug), can aid the device in distributing the fragrance into the room.

FIGS. 3 and 4 show the distance between the top 17 of the distal chimney extension and the top surface 11 of the device.

Figure 6:
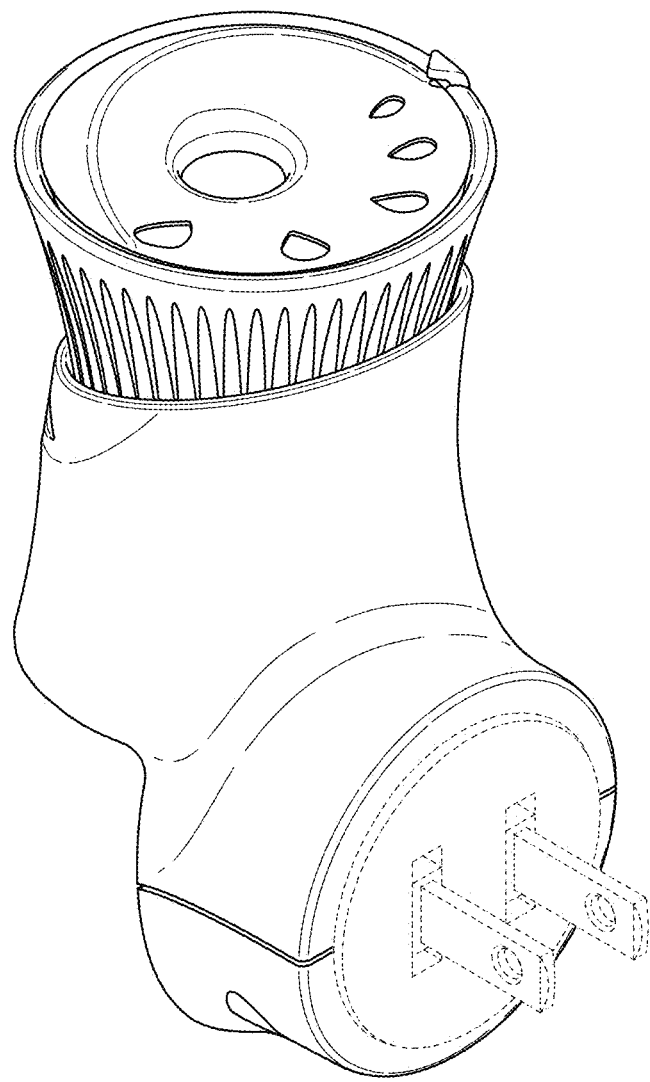
Figure 7:
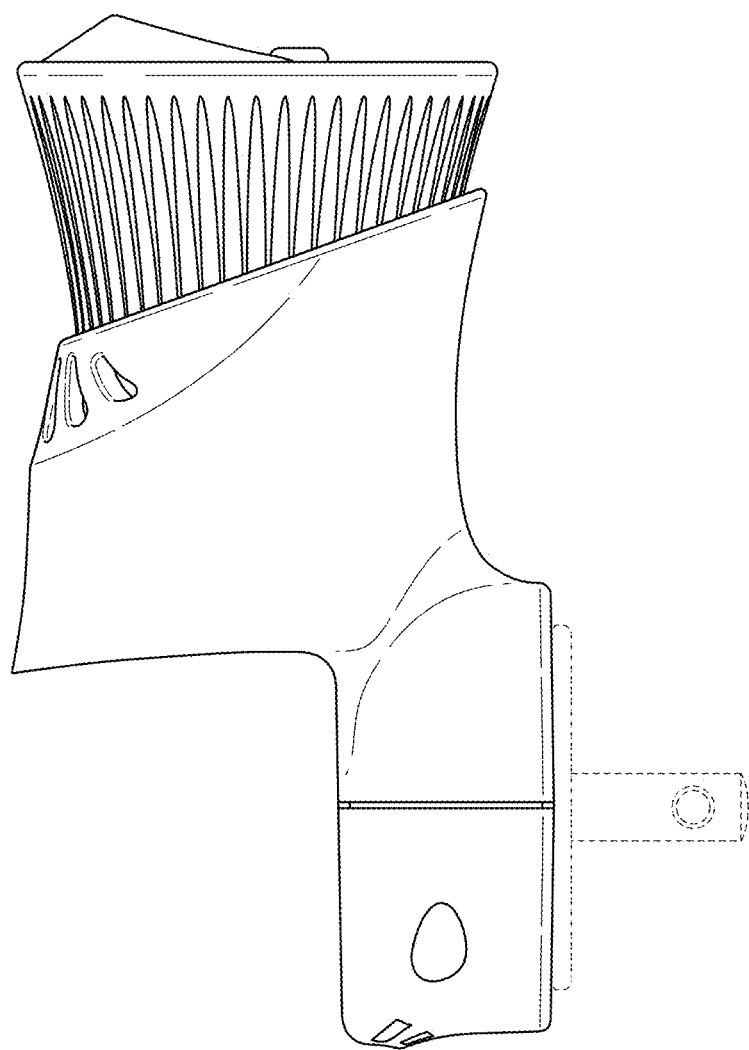
Figure 8:
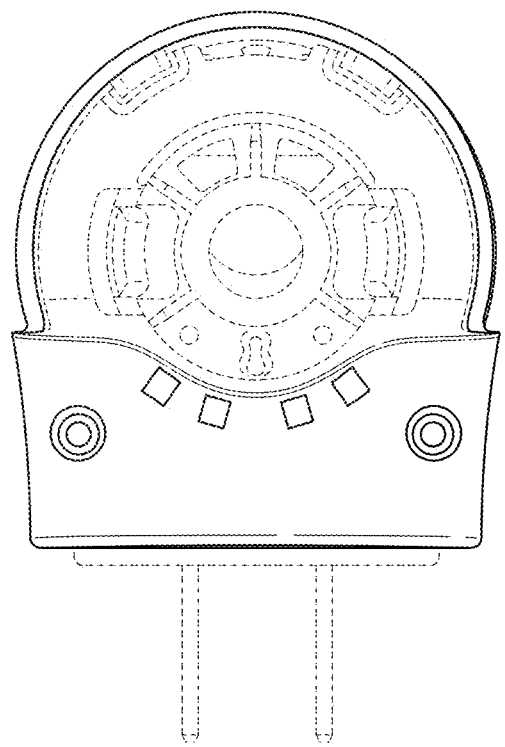

FIGS. 6, 7 and 8 show isometric, side and bottom views, respectively, of an embodiment according to the present invention.

Preferably, and as shown in FIGS. 6 to 8, the invention comprises one or more vents that permit the flow of air into the device. Advantageously, the vent(s) is/are positioned on the front of the device.

Without wishing to be bound by theory, it is believed that the presence of one or more air vents allows air to be drawn into the device and increases the momentum of the active-laden air. This results in the actives being distributed throughout the room with increased speed and efficiency.

In a further aspect of the invention the distal chimney extension 15 is separable from the main chimney 6 and formed of a discrete component.

In a further aspect of the invention the discrete component may be mounted onto the top surface of the housing.

In a further aspect of the invention the discrete component may be mounted onto a regular opening chimney to form the non-regular external opening of the chimney.

In a further aspect of the invention the discrete component forms the entire top portion of the device housing.

In a further aspect of the invention the chimney 6 is substantially uniform in dimensions along its length from the base 14 to the lowest opening point of the external opening 7.

In a further aspect of the invention the chimney 6 is substantially cylindrical in shape between to the chimney base 13 and external opening 7.

The chimney 6 may also be completely irregular in shape. In this situation, the dimensions of the distal chimney extension 15 may be related to the size of opening 7. Preferably the length ratio of the length of the distal chimney extension surface 16 to the largest diameter of opening 7, is between 1:10 and 10:1. The angle θ of the distal chimney extension may be also, alternatively, measured against the vertical plane when the device is plugged into a wall socket.

The device may be used with any suitable liquid electrical vaporiser composition known from the art. The skilled person will be aware of the vast range of possibilities.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is also described in the following non-limiting Examples.

EXAMPLES

Fragrance Distribution

It was determined analytically whether the present invention distributes fragrance throughout a room. Air samples at four corners of a room were taken prior to testing. A working device according to the present invention emanating fragrance was then operated and the relative fragrance concentration at each of the four corners of the room was calculated.

By statistically comparing the relative concentration of specific fragrance components in all four corners of the room, the distribution or 'spread' of the fragrance can be inferred.

Definitions

TD—thermal desorption
GC MS—gas chromatograph with mass spectral detector
PTFE—polytetrafluoroethylene
MSDS—material safety data sheet
ANOVA—Analysis of variation. The F ratio is the probability produced by an ANOVA and can determine whether differences in a set of counts or measurements were most likely due to chance variation, thus determining whether data sets are significantly different to one another statistically. If the F number generated is larger than the $F_{crit}$ value, the data sets are significantly different to one another.

Equipment

Test Chamber: 28 $m^3$ controlled booths
Stainless steel sorbent tube with Tenax TA sorbent
Gilian LFS-113DC low flow sampling pumps
PTFE tubing
Gilian Gilibrator 2 Primary Flow Calibrator with Gilian low flow cell
Agilent 7890 GC with a 5975 Inert MSD and Markes Ultra/Unity TD system Methodology Background samples were taken before fragrance air sampling began. A Tenax tube was placed at each of the four corners of a 28 m³ large sensory booth for each sampling session and the booth was set to the test conditions of: 22+/−2° C. and 55+/−5% RH.

The pumps were switched on to sample the air in each of the four corners for 10 minutes (around 2 litres of air were drawn through each tube during sampling).

Once background testing was complete, a liquid electrical device according to the invention and fitted with a fragrance refill is plugged into the socket located within the booth. The device was set to minimum setting operated for 1 hour prior to air sampling. This was carried out for three distinct fragrances (Fragrance A to C) obtained from a commercial fragrance house.

After an hour the Tenax tubes were thermally desorbed and analysed using an Agilent 7890 GC with a 5975 Inert MSD and Markes Ultra/Unity TD system. Each of the three fragrances contain known chemical components, which were tested for using the Agilent 7890 GC.

Results

TABLE 1

| Fragrance A Components | F | Fcrit | P-value |
| --- | --- | --- | --- |
| A1 | 0.010853 | 3.098391 | 0.998398 |
| A2 | 0.117635 | | 0.948699 |
| A3 | 0.037105 | | 0.990141 |
| A4 | 0.017890 | | 0.996634 |
| A5 | 0.014041 | | 0.997650 |
| A6 | 0.034788 | | 0.991029 |
| A7 | 0.052608 | | 0.983618 |
| A8 | 0.028276 | | 0.993382 |
| A9 | 0.190465 | | 0.901643 |

As the F value is lower than that of the $F_{crit}$ value for all 9 fragrance components, there is no significant difference in the relative concentration of the fragrance in any of the four corners of the room. As there is no difference in the relative concentrations, the four corners of the room are equivalent and thus the fragrance is evenly distributed. This result was seen within the 90% confidence interval ($P \geq 0.9$).

TABLE 2

| Fragrance B Components | F | Fcrit | P-value |
| --- | --- | --- | --- |
| B1 | 0.005543 | 3.098391 | 0.999412 |
| B2 | 0.032938 | | 0.991719 |
| B3 | 0.245516 | | 0.863528 |
| B4 | 0.031618 | | 0.992201 |
| B5 | 0.024016 | | 0.994797 |
| B6 | 0.170873 | | 0.914802 |
| B7 | 0.049757 | | 0.984887 |
| B8 | 0.075164 | | 0.972655 |
| B9 | 0.244802 | | 0.864030 |

As the F value is lower than that of the $F_{crit}$ value for all 9 fragrance components, there is no significant difference in the relative concentration of the fragrance in any of the four corners of the room. As there is no difference in the relative concentrations, the four corners of the room are equivalent and thus the fragrance is evenly distributed. This result was seen within the 90% confidence interval ($P \geq 0.9$) for 8 of the 9 components.

TABLE 3

| Fragrance C Components | F | Fcrit | P-value |
| --- | --- | --- | --- |
| C1 | 0.07168 | 3.09839 | 0.97444 |
| C2 | 0.04327 | | 0.98766 |

TABLE 3-continued

| Fragrance C Components | F | Fcrit | P-value |
| --- | --- | --- | --- |
| C3 | 0.01377 | | 0.99772 |
| C4 | 0.08579 | | 0.96701 |
| C5 | 0.18724 | | 0.90383 |
| C6 | 0.07247 | | 0.97404 |
| C7 | 0.03859 | | 0.98956 |
| C8 | 0.11103 | | 0.95265 |
| C9 | 0.09719 | | 0.96067 |
| C10 | 0.08079 | | 0.96970 |

As the F value is lower than that of the $F_{crit}$ value for 10 components, there is no significant difference in the relative concentration of the fragrance in any of the four corners of the room. As there is no difference in the relative concentrations, the four corners of the room are equivalent and so the fragrance is evenly distributed. This result was seen within the 90% confidence interval ($P \geq 0.9$).

Computation Fluid Dynamics

Figure 9:
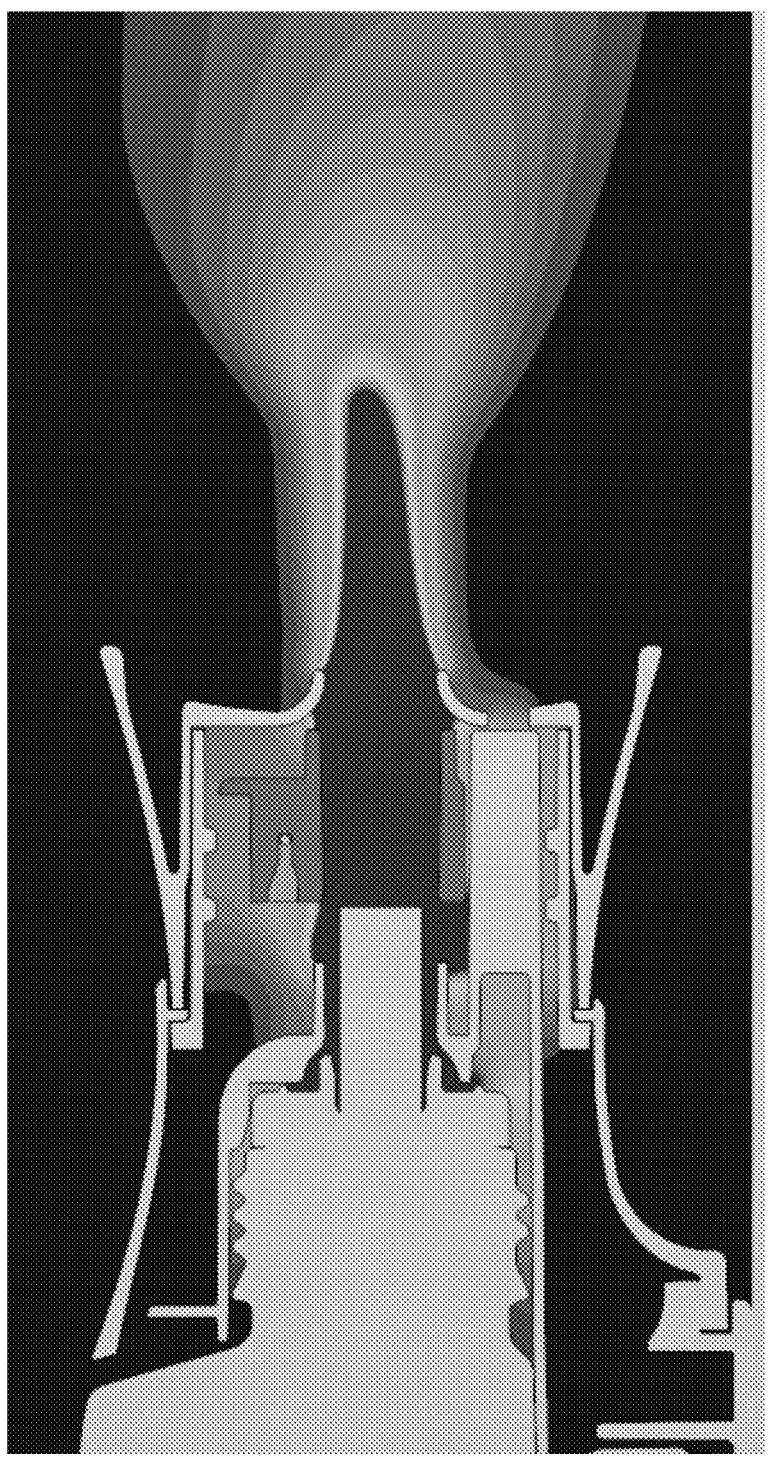
Figure 10:
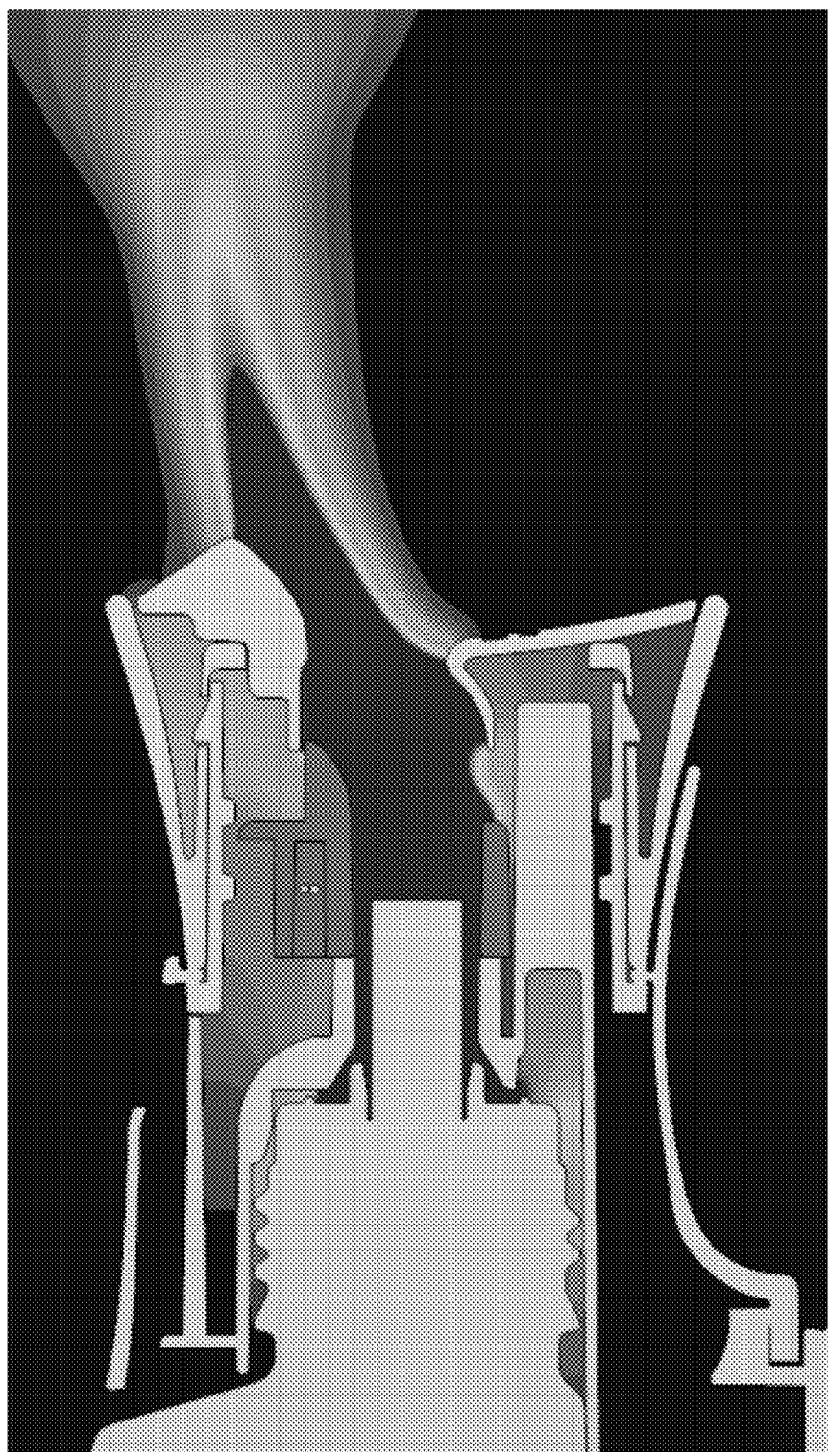

Using Siemens Computational Software (STAR-CCM—version 13.02) the flow of the active-laden air was modelled for both a standard plug in vaporiser and a vaporiser according the present invention. The respective direction of the flows are shown in FIGS. 9 (standard device) and 10 (present invention).

It can be seen that the active-laden air is drawn into the room with the use of a vaporizer according to the present invention.

The Uniformity Index of the fragrance compositions were modelled at 25 cm and 50 cm above the device. The closer the Uniformity index to 1, the more uniformly the fragrance is emanating away from the device.

TABLE 4

| Height above the device | Device Setting | Standard Device Uniformity Index | Invention Uniformity Index | Percentage Difference Invention vs Standard |
| --- | --- | --- | --- | --- |
| 25 cm | Min | 0.254 | 0.326 | 24.82% |
| | Max | 0.259 | 0.326 | 22.91% |
| 50 cm | Min | 0.342 | 0.448 | 26.83% |
| | Max | 0.348 | 0.448 | 25.13% |

Table 4 demonstrates how a vaporizer according to the present invention results in a significantly more uniform distribution of fragrance.

The Computational Fluid Dynamics calculations support the empirical results and demonstrate that the inclusion of the distal chimney extension has a potent effect on directing the heated stream of active laden air away from the wall and out into the room relative to a standard plug in device.

The invention is defined by the claims.

The invention claimed is:

1. A liquid electric vaporiser comprising:
   a housing;
   a plug, configured to engage with a mains electricity socket, located on one side of the housing;
   a chimney extending between a base to an external opening at the top of the housing which comprises an inner surface and further wherein the chimney has a distal side with a distal inner surface and a proximal side with a proximal inner surface relative to the plug;
   a heating means, located adjacent the chimney;
   a detachable refill bottle which engages with the housing, the refill bottle having a wick in fluid communication with a material to be dispensed therefrom; and the wick extending from the bottle into the chimney in proximity with said heating means when the refill bottle is engaged with the housing;

and wherein the external opening of the chimney comprises a distal chimney extension which extends beyond a part of the external opening to a distal chimney extension top, such that the length on the distal side of the chimney as measured between the base and along the distal inner surface of the chimney to the distal chimney extension top is greater than on the proximal side of the chimney as measured from the base along the proximal inner surface of the chimney to the lowest point of the external opening.

2. The liquid electric vaporiser of claim 1 wherein the distal chimney extension is angled away from the plug.

3. The liquid electric vaporiser of claim 2 wherein the angle between a distal chimney extension surface of the distal chimney extension and the distal side of the chimney is at least 15 degrees.

4. The liquid electric vaporiser of claim 3, wherein the distal chimney extension surface has a convex inner surface.

5. The liquid electric vaporiser of claim 3, wherein the distal chimney extension surface has a flat inner surface.

6. The liquid electric vaporiser of claim 1, wherein the distal chimney extension between the external opening and the distal chimney extension top when measured along a distal chimney extension surface is between 5 and 50% of the length of the chimney from the base to the lowest point of the external opening.

7. The liquid electric vaporiser of claim 1, wherein the distal chimney extension is formed of a discrete component attachable to the top of the housing.

8. The liquid electric vaporiser according to claim 7 wherein the discrete component is mounted onto a surface at the top of the housing.

9. The liquid electric vaporiser of claim 1, wherein the chimney is substantially cylindrical in at the external opening.

10. The liquid electric vaporiser of claim 3 wherein the angle of the chimney extension away from the chimney is at least 25 degrees.

11. The liquid electric vaporiser of claim 10 wherein the angle of the chimney extension away from the chimney is at least 30 degrees.

12. The liquid electric vaporiser of claim 11 wherein the angle of the chimney extension away from the chimney is at least 40 degrees.

13. The liquid electric vaporiser of claim 6, wherein the distal chimney extension is between 5 and 20% of the length of the chimney below the lowest point of external opening.

14. The liquid electric vaporiser of claim 13, wherein the distal chimney extension is between 7 and 15% of the length of the chimney below the lowest point of external opening.

15. The liquid electric vaporiser of claim 1, wherein the chimney extending between the base to the external opening at the top of the housing is substantially straight between the base and the external opening.

16. The liquid electric vaporiser of claim 1, wherein the chimney extending between the base to the external opening at the top of the housing includes a first part and a second part which is angled with respect to the first part, wherein the first part extends from the base, and the second part extends to the external opening.

17. The liquid electric vaporiser of claim 16, wherein the external opening is distal relative to the plug and also relative to the first part of the chimney.

* * * * *